United States Patent
Kawahara et al.

(10) Patent No.: US 7,816,541 B2
(45) Date of Patent: Oct. 19, 2010

(54) PROCESS FOR PRODUCING AN OPTICALLY ACTIVE COMPOUND

(75) Inventors: Shigeru Kawahara, Kanagawa (JP); Yusuke Amino, Kanagawa (JP); Masakazu Sugiyama, Kanagawa (JP)

(73) Assignee: Ajinomoto Co., Inc., Tokyo (JP)

(*) Notice: Subject to any disclaimer, the term of this patent is extended or adjusted under 35 U.S.C. 154(b) by 433 days.

(21) Appl. No.: 12/028,360

(22) Filed: Feb. 8, 2008

(65) Prior Publication Data

US 2008/0207920 A1  Aug. 28, 2008

Related U.S. Application Data

(60) Provisional application No. 60/888,967, filed on Feb. 9, 2007.

(30) Foreign Application Priority Data

Feb. 8, 2007  (JP) ............................... 2007-029179

(51) Int. Cl.
*C07D 209/04* (2006.01)
(52) U.S. Cl. ...................................... 548/494; 548/469
(58) Field of Classification Search ................. 548/469, 548/494
See application file for complete search history.

(56) References Cited

U.S. PATENT DOCUMENTS

| | | | |
|---|---|---|---|
| 5,994,559 A | 11/1999 | Abushanab et al. | |
| 7,064,219 B2 * | 6/2006 | Kawahara et al. | 548/495 |
| 7,241,599 B2 | 7/2007 | Sugiyama et al. | |
| 7,297,800 B2 | 11/2007 | Sugiyama et al. | |
| 7,351,569 B2 | 4/2008 | Sugiyama et al. | |
| 7,371,549 B2 | 5/2008 | Sugiyama et al. | |
| 7,390,909 B2 * | 6/2008 | Kawahara et al. | 548/495 |
| 7,396,941 B2 * | 7/2008 | Mori et al. | 548/495 |
| 7,402,412 B2 | 7/2008 | Sugiyama et al. | |
| 7,432,100 B2 | 10/2008 | Sugiyama et al. | |
| 7,534,590 B2 | 5/2009 | Mori et al. | |
| 7,534,898 B2 * | 5/2009 | Amino et al. | 548/495 |
| 7,572,607 B2 | 8/2009 | Hicks et al. | |
| 7,582,455 B2 | 9/2009 | Brazeau et al. | |
| 7,612,214 B2 | 11/2009 | Amino et al. | |
| 2004/0063175 A1 | 4/2004 | Abraham et al. | |
| 2005/0020508 A1 | 1/2005 | Amino et al. | |
| 2005/0106305 A1 | 5/2005 | Abraham et al. | |
| 2005/0112260 A1 | 5/2005 | Abraham et al. | |
| 2005/0170041 A1 | 8/2005 | Abraham et al. | |
| 2005/0221455 A1 | 10/2005 | McFarlan et al. | |
| 2005/0244937 A1 | 11/2005 | Abraham et al. | |
| 2005/0272939 A1 | 12/2005 | Amino et al. | |
| 2005/0282260 A1 | 12/2005 | Hicks et al. | |
| 2006/0003426 A1 | 1/2006 | Sugiyama et al. | |
| 2006/0009394 A1 | 1/2006 | Amino | |
| 2006/0074249 A1 | 4/2006 | Kawahara et al. | |
| 2006/0252135 A1 | 11/2006 | Brazeau et al. | |
| 2007/0072277 A1 | 3/2007 | Sugiyama et al. | |
| 2007/0099277 A1 | 5/2007 | Anderson et al. | |
| 2007/0105938 A1 | 5/2007 | Anderson et al. | |
| 2008/0020434 A1 | 1/2008 | Brazeau et al. | |
| 2008/0020435 A1 | 1/2008 | Burke et al. | |
| 2008/0193975 A1 | 8/2008 | Sugiyama et al. | |
| 2008/0193984 A1 | 8/2008 | Sugiyama et al. | |
| 2008/0199921 A1 | 8/2008 | Sugiyama et al. | |
| 2008/0274518 A1 | 11/2008 | Hicks et al. | |
| 2008/0318290 A1 | 12/2008 | Sugiyama et al. | |
| 2009/0117625 A1 | 5/2009 | Abraham et al. | |
| 2009/0259052 A1 | 10/2009 | Kawahara et al. | |

FOREIGN PATENT DOCUMENTS

| | | |
|---|---|---|
| CN | 1749402 A | 3/2006 |
| JP | 2002-60382 | 2/2002 |
| JP | 2004-331650 | 11/2004 |
| WO | WO 03/056026 A1 | 7/2003 |
| WO | WO 03/059865 A1 | 7/2003 |
| WO | WO 2004-067494 A1 | 8/2004 |

OTHER PUBLICATIONS

U.S. Appl. No. 12/613,713, filed Nov. 6, 2009, Kawahara, et al.
Kozo Nakamura, et al., "Total Synthesis of Monatin", Organic Letters, vol. 2, No. 19, Aug. 25, 2000, pp. 2967-2970.
Cedric W. Holzapfel, et al. "A Simple Cycloaddition Approach to a Racemate of the Natural Sweetener Monatin", Synthetic Communications, vol. 24, No. 22, 1994, pp. 3197-3211.
Cedric W. Holzapfel, et al. "The Synthesis of A γ-Keto-α-Amino Acid, A Key Intermediate in the Synthesis of Monatin, a New Natural Sweetener", Synthetic Communications, vol. 23, No. 18, 1993, pp. 2511-2526.
Davi de Jesus Oliveira, et al., "Diastereoselective formation of a quaternary center in a pyroglutamate derivative. Formal synthesis of Monatin", Tetrahedron Letters, vol. 42, 2001, pp. 6793-6796.
Nicholas Gathergood, et al., "Direct catalytic asymmetric aldol reactions of pyruvates: scope and mechanism", Org. Biomol. Chem., vol. 2, 2004, pp. 1077-1085.
Karsten Juhl, et al., "Catalytic asymmetric homo-aldol reaction of pyruvate—a chiral Lewis acid catalyst that mimics aldolase enzymes", Chem. Commun., 2000, pp. 2211-2212.
Paolo Dambruoso, et al., "Efficiency in Isotetronic Acid Synthesis via a Diamine—Acid Couple Catalyzed Ethyl Pyruvate Homoaldol Reaction", Organic Letters, vol. 7, No. 21, 2005, pp. 4657-4660.
U.S. Appl. No. 11/951,395, filed Dec. 6, 2007, Kawahara, et al.
U.S. Appl. No. 12/613,839, filed Nov. 6, 2009, Sugiyama, et al.
105,696, filed Jun. 25, 2009, Kawahara, et al.

* cited by examiner

*Primary Examiner*—Golam M Shameem
(74) *Attorney, Agent, or Firm*—Oblon, Spivak, McClelland, Maier & Neustadt, L.L.P.

(57) ABSTRACT

The present invention provides a process for selectively producing an enantiomer at position 4 of an optically active compound in the cross aldol reaction of pyruvic acid and indole-3-pyruvic acid. The process comprises the step of reacting pyruvic acid with indole-3-pyruvic acid in the presence of an optically active α-amino acid containing a secondary amine and a metal ion.

16 Claims, No Drawings

SEQUENCE LISTING

```
<160> NUMBER OF SEQ ID NOS: 6

<210> SEQ ID NO 1
<211> LENGTH: 1709
<212> TYPE: DNA
<213> ORGANISM: Bacillus macerans
<220> FEATURE:
<221> NAME/KEY: CDS
<222> LOCATION: (630)..(1481)

<400> SEQUENCE: 1
tacatcaggt agcgccatgc atgacagaaa gggatcatga gcgttatctg ctgcgtttac      60
aacagagtga cgactgagtc agagcaattg tcgactttat cgcagaggtt tttatcagga     120
tcattatgcc atcagcttga gttgcaattc gaggatgcca tgtctggtca gacaacatta     180
aatccaggca ttgttagcta tgatgtcagt aaaggtggca gtttagtgat tagtatgcgc     240
tattctgtgt cctatccatt cgatgaaaaa ttacggaggc tcaacgttta gttgtaaaaa     300
gaggattttc attagatatt caagacgact ccaagcccca ttatgtcagt gaagatgatc     360
catttatcca aacattagcg gctatttata gacgtcaatc aggagataca gaaacaccgt     420
tattatctac aggtggtgga acgtatgcac gtgtgctgaa aaaaggcgtg gcctttggca     480
tgctattccc tggggagcag gatgtggcgc atcggcgga tgagtttgta gtgattgaaa     540
atcttgtaaa agcagcggct atttatgcgg aagcaattgt tgagcttgcg ggaaaaaaat     600
aacataaaga cgaaaggat gaacggaaaa atg gca tat tca tta tgg aat gat       653
                                   Met Ala Tyr Ser Leu Trp Asn Asp
                                   1               5 caa att gtt gaa gaa gga tct att gca atc tca cca gaa gac aga ggt       701
Gln Ile Val Glu Glu Gly Ser Ile Ala Ile Ser Pro Glu Asp Arg Gly
     10              15                  20 tat cag ttt ggt gac ggt att tat gaa gta att aaa gtt tat aac gga       749
Tyr Gln Phe Gly Asp Gly Ile Tyr Glu Val Ile Lys Val Tyr Asn Gly
25                  30                  35                  40 aat atg ttt aca gca caa gag cac att gat cgt ttc tat gcg agc gcc       797
Asn Met Phe Thr Ala Gln Glu His Ile Asp Arg Phe Tyr Ala Ser Ala
             45                  50                  55 gaa aaa att cgc ctt gtt atc cct tat aca aaa gat gtt tta cac aag       845
Glu Lys Ile Arg Leu Val Ile Pro Tyr Thr Lys Asp Val Leu His Lys
         60                  65                  70 tta cta cat gag cta att gaa aag aat aat cta gaa aca gga cat gtt       893
Leu Leu His Glu Leu Ile Glu Lys Asn Asn Leu Glu Thr Gly His Val
     75                  80                  85 tat ttt caa atc act cgt ggg gct aat tca cgt aat cac gtt ttc ccg       941
Tyr Phe Gln Ile Thr Arg Gly Ala Asn Ser Arg Asn His Val Phe Pro
 90                  95                 100 gat gca agt att cct gct gta tta act gga aat gta aaa gcg ggt gaa       989
Asp Ala Ser Ile Pro Ala Val Leu Thr Gly Asn Val Lys Ala Gly Glu
105                 110                 115                 120 cgt gca tat gaa aac ttt gaa aaa ggt gtt aaa gcc act ttt gtt gag      1037
Arg Ala Tyr Glu Asn Phe Glu Lys Gly Val Lys Ala Thr Phe Val Glu
                125                 130                 135
```

```
gat att cgt tgg ttg cgt tgt gac att aaa tct tta aac ttg ctt ggt      1085
Asp Ile Arg Trp Leu Arg Cys Asp Ile Lys Ser Leu Asn Leu Leu Gly
        140                 145                 150 gca gta tta gca aaa caa gaa gct gcg gag aaa ggt tgt tat gaa gcg      1133
Ala Val Leu Ala Lys Gln Glu Ala Ala Glu Lys Gly Cys Tyr Glu Ala
            155                 160                 165 atc tta cat cgc gga gat atc gtg aca gaa tgc tct tca gct aat gtt      1181
Ile Leu His Arg Gly Asp Ile Val Thr Glu Cys Ser Ser Ala Asn Val
    170                 175                 180 tac gga att aaa gat gga aaa ctt tat aca cat cca gct aat aat ttc      1229
Tyr Gly Ile Lys Asp Gly Lys Leu Tyr Thr His Pro Ala Asn Asn Phe
185                 190                 195                 200 atc tta aat ggt att aca cgt caa gtc att tta aaa tgt gcg gaa gaa      1277
Ile Leu Asn Gly Ile Thr Arg Gln Val Ile Leu Lys Cys Ala Glu Glu
                205                 210                 215 att aat tta cca gta atc gaa gag cca atg acg aaa gct gat tta cta      1325
Ile Asn Leu Pro Val Ile Glu Glu Pro Met Thr Lys Ala Asp Leu Leu
        220                 225                 230 aca atg gat gaa atc att gtg tcg tct gta tct tct gag gtt acg cca      1373
Thr Met Asp Glu Ile Ile Val Ser Ser Val Ser Ser Glu Val Thr Pro
            235                 240                 245 gtc att gat gtg gac ggc aac caa att ggg gct gga gtt ccc ggt gaa      1421
Val Ile Asp Val Asp Gly Asn Gln Ile Gly Ala Gly Val Pro Gly Glu
    250                 255                 260 tgg act cgt caa tta cag caa tca ttt gaa gcg aaa tta cca ctt tca      1469
Trp Thr Arg Gln Leu Gln Gln Ser Phe Glu Ala Lys Leu Pro Leu Ser
265                 270                 275                 280 atg aat acc aaa taaagaacc ttgtagagaa ctatctgtat ggatagttct           1521
Met Asn Thr Lys ctttatttat gggtgtaatg ttgggtctcg tcatgtaaaa taaaaggat agtagaataa     1581 tcttacagat tgaaatttgt agagcaatgt cgatgtaatg aatacataag aatgcataga    1641
ctctttttac aaaggggatc gagaaaaaag agaactaaag agatggtaag taagaatgga    1701
gtgacctt                                                             1709

<210> SEQ ID NO 2
<211> LENGTH: 284
<212> TYPE: PRT
<213> ORGANISM: Bacillus macerans

<400> SEQUENCE: 2

Met Ala Tyr Ser Leu Trp Asn Asp Gln Ile Val Glu Glu Gly Ser Ile
1               5                   10                  15

Ala Ile Ser Pro Glu Asp Arg Gly Tyr Gln Phe Gly Asp Gly Ile Tyr
            20                  25                  30

Glu Val Ile Lys Val Tyr Asn Gly Asn Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Glu Leu Ile Glu Lys
65                  70                  75                  80

Asn Asn Leu Glu Thr Gly His Val Tyr Phe Gln Ile Thr Arg Gly Ala
                85                  90                  95

Asn Ser Arg Asn His Val Phe Pro Asp Ala Ser Ile Pro Ala Val Leu
            100                 105                 110

Thr Gly Asn Val Lys Ala Gly Glu Arg Ala Tyr Glu Asn Phe Glu Lys
        115                 120                 125
```

```
Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

Ala Glu Lys Gly Cys Tyr Glu Ala Ile Leu His Arg Gly Asp Ile Val
                165                 170                 175

Thr Glu Cys Ser Ser Ala Asn Val Tyr Gly Ile Lys Asp Gly Lys Leu
            180                 185                 190

Tyr Thr His Pro Ala Asn Asn Phe Ile Leu Asn Gly Ile Thr Arg Gln
                195                 200                 205

Val Ile Leu Lys Cys Ala Glu Glu Ile Asn Leu Pro Val Ile Glu Glu
        210                 215                 220

Pro Met Thr Lys Ala Asp Leu Leu Thr Met Asp Glu Ile Ile Val Ser
225                 230                 235                 240

Ser Val Ser Ser Glu Val Thr Pro Val Ile Asp Val Asp Gly Asn Gln
                245                 250                 255

Ile Gly Ala Gly Val Pro Gly Glu Trp Thr Arg Gln Leu Gln Gln Ser
            260                 265                 270

Phe Glu Ala Lys Leu Pro Leu Ser Met Asn Thr Lys
                275                 280
```

```
<210> SEQ ID NO 3
<211> LENGTH: 40
<212> TYPE: DNA
<213> ORGANISM: Artificial Sequence
<220> FEATURE:
<223> OTHER INFORMATION: mutagenic sense primer for S243N

<400> SEQUENCE: 3
gaaatcattg tgtcgtctgt aaattctgag gttacgccag                40

<210> SEQ ID NO 4
<211> LENGTH: 40
<212> TYPE: DNA
<213> ORGANISM: Artificial Sequence
<220> FEATURE:
<223> OTHER INFORMATION: mutagenic anti-sense primer for S243N

<400> SEQUENCE: 4
ctggcgtaac ctcagaattt acagacgaca caatgatttc                40

<210> SEQ ID NO 5
<211> LENGTH: 40
<212> TYPE: DNA
<213> ORGANISM: Artificial Sequence
<220> FEATURE:
<223> OTHER INFORMATION: mutagenic sense primer for A182S

<400> SEQUENCE: 5
gtgacagaat gctcttcatc taatgtttac ggaattaaag                40

<210> SEQ ID NO 6
<211> LENGTH: 40
<212> TYPE: DNA
<213> ORGANISM: Artificial Sequence
<220> FEATURE:
<223> OTHER INFORMATION: mutagenic anti-sense primer for A182S-AS

<400> SEQUENCE: 6
ctttaattcc gtaaacatta gatgaagagc attctgtcac                40
```

PROCESS FOR PRODUCING AN OPTICALLY ACTIVE COMPOUND

CROSS REFERENCES TO RELATED APPLICATIONS

This application is claims priority to U.S. Provisional Application No. 60/888,967, filed on Feb. 9, 2007, and Japanese Patent Application No. 2007-029179, filed on Feb. 8, 2007, both of which are incorporated herein by reference in their entireties.

BACKGROUND OF THE INVENTION

1. Field of the Invention

The present invention relates to a process for producing an optically active compound.

2. Discussion of the Background 3-(1-Amino-1,3-dicarboxy-3-hydroxy-butan-4-yl)-indole (hereinafter referred to as "monatin") is contained in the root of *Scherochitoma ilicifolius*, and its sweetness is several hundred times as high as sucrose. Thus this compound is expected to be a low calorie sweetener (see, JP Patent Kokai Publication No. JP-A-64-25757).

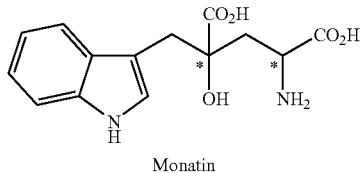

Monatin

In this specification, the term "monatin" is used as the generic designation for the four types of stereoisomers without being limited to the (2S,4S)-isomer. Thus, the designation of "monatin" means at least one of (2S,4S)-, (2S,4R)-, (2R,4S)- and (2R,4R)-isomers of monatin, except in the a case when it is used for limiting to a particular isomer.

For the synthesis of monatin, nine cases have been reported:

(1) the method as described in *Organic Letters*, vol. 2, no. 19, pp. 2967-2970 (2000);

(2) the method as disclosed in U.S. Pat. No. 5,994,559;

(3) the method as described in *Synthetic Communication*, vol. 24, no. 22, pp. 3197-3211 (1994);

(4) the method as described in *Synthetic Communication*, vol. 23, no. 18, pp. 2511-2526 (1993);

(5) the method as described in *Tetrahedron Letters*, vol. 42, no. 39, pp. 6793-6796 (2001);

(6) the method as described in Japanese Patent Kokai Publication No. JP-P2002-060382A;

(7) the method as described in Japanese Patent Kokai Publication No. JP-P2004-331650A;

(8) the procedure as described in WO2004/067494A1; and (9) the procedure as described in WO2003/059865A1.

Particularly, in the procedure as described in WO2003/059865A1, optically active monatin can be produced in a short process from pyruvic acid and indole-3-pyruvic acid, and so it is a commercially excellent process.

However, since the intermediate for production, i.e., 4-hydroxy-4-(3-indolylmethyl)-2-hydroxyiminoglutaric acid, is obtained as the racemate at the 4 position, it has to be resolved optically, and the undesired enantiomer at the 4 position has to be recycled. Therefore, an additional improvement has been required.

As an example of an improvement, an asymmetric cross aldol reaction utilizing an enzyme (aldolase) has been reported in, for example, WO2003/056026. According to these enzymatic procedures, a highly optically pure 4-hydroxy-4-(3-indolylmethyl)-2-ketoglutaric acid can be synthesized from pyruvic acid and indole-3-pyruvic acid even though in low yield.

So far, in the asymmetric cross aldol reaction using an α-keto acid ester as a donor and acceptor, it has been reported that the enantiomeric induction was achieved only in three cases. That is, the procedures are described in the following documents:

(1) The procedure as described in *Organic & Biomolecular Chemistry*, vol. 2, pp. 1077-1085 (2004);

(2) The procedure as described in *Chemical Communications*, pp. 2211-2212 (2000); and (3) The procedure as described in *Organic Letters*, vol. 7, no. 21, pp. 4657-4660 (2005).

The methods as described in the above-mentioned documents, however, employed α-keto acid esters as donors in every cases, and accordingly cannot be applied to production of monatin in which a free α-keto acid, pyruvic acid, is used as a donor. In particular, in the procedure described in *Chemical Communications*, pp. 2211-2212 (2000) and *Organic Letters*, vol. 7, no. 21, pp. 4657-4660 (2005), only the dimerization of ethyl pyruvate is mentioned, but there is no description of the asymmetric cross aldol reaction using different pyruvic acids as donor and acceptor in the production of monatin. *Organic & Biomolecular Chemistry*, vol. 2, pp. 1077-1085 (2004) describes the asymmetric cross aldol reaction using different pyruvic acid esters. In this reaction, however, ethyl trifluoropyruvate as an α-keto acid ester is used as an acceptor which has no active hydrogen, and accordingly it cannot be applied to the production of monatin using indole-3-pyruvic acid as an acceptor which has an active hydrogen.

Thus, there is no report on an asymmetric catalyst which is capable of discriminating pyruvic acid and indole-3-pyruvic acid as a donor and an acceptor, respectively, which are required in production of monatin, indicating that it was difficult in view of the current level of technology. All of the raw materials have an active hydrogen at the α-position of the carbonyl group and can act as donor or acceptor; this makes it difficult to control the reaction site. This difficulty would easily be understood among the persons skilled in the art.

Thus, there remains a need for a process for selectively producing the enantiomer at the 4 position in the cross aldol reaction of pyruvic acid and indole-3-pyruvic acid.

SUMMARY OF THE INVENTION

Accordingly, it is one object of the present invention to provide novel processes for selectively producing an enantiomer at the 4 position in the cross aldol reaction of pyruvic acid and indole-3-pyruvic acid.

It is another object of the present invention to provide novel methods for producing optically active monatin.

These and other objects, which will become apparent during the following detailed description, have been achieved by the inventors' discovery that the presence of an optically active α-amino acid containing a secondary amine and a metal ion while carrying out the cross aldol reaction of pyruvic acid with an indole-3-pyruvic acid leads to the solution of the above problem.

Thus, the present invention provides:

(1) A process for producing an optically active compound of the following formula (3) (including a salt form) which comprises reacting a pyruvic acid of the following formula (1) with an indole-3-pyruvic acid of the following formula (2) in the presence of an optically active α-amino acid containing a secondary amine and a metal ion.

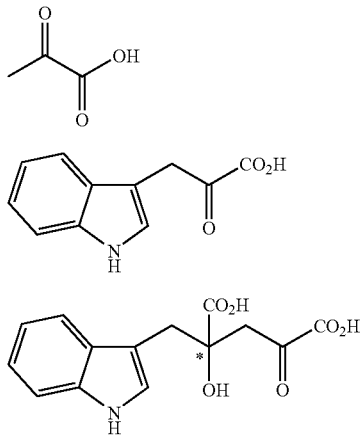

wherein the asterisk in the formula (3) indicates an asymmetric carbon.

(2) A process for producing an optically active compound of the following general formula (5) (including a salt form) which comprises making an amine derivative of the general formula (4) or a salt thereof act of the optically active compound obtained by the process as described in (1).

NH$_2$OR (4)

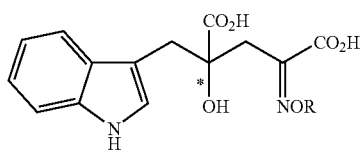

wherein the asterisk in the formula (5) indicates an asymmetric carbon, and R represents a hydrogen atom or methyl group.

(3) The process for producing an optically active compound (including a salt form) as described in (1), wherein the optically active α-amino acid containing a secondary amine is one or more selected from hydroxyproline and proline.

(4) The process for producing an optically active compound (including a salt form) as described in (1), wherein the optically active α-amino acid containing a secondary amine is represented by the following general formula (6).

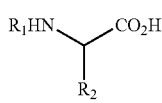

wherein $R_1$ represents an alkyl group having 1 to 3 carbon atoms; $R_2$ represents an alkyl group having 1 to 6 carbon atoms or an aralkyl group having 7 to 10 carbon atoms, in which the alkyl or aryl group may be substituted by at least one hydroxyl or amino group.

(5) The process for producing an optically active compound (including a salt form) as described in (1), wherein the metal ion is one or more selected from magnesium (II) ion, zinc (II) ion, cobalt (II) ion, cobalt (III) ion, and nickel (II) ion.

(6) The process for producing an optically active compound (including a salt form) as described in (1), wherein the pH of the reaction mixture during the reaction is 7 to 12.

(7) A process for producing monatin or a salt thereof which comprises the process for producing the optically active compound (including a salt form) as described in any of (1) to (6).

(8) A process for producing monatin or a salt thereof which comprises the step of further reacting the optically active compound produced by the process of any one of claims 1 to 6 with a transaminase and an amino donor.

The meritorious effects of the present invention are summarized as follows. The invention provides a new efficient procedure for an asymmetric cross aldol reaction. This procedure is applicable to the preparation of optical active compounds in addition to an optically active monatin known as a sweetener.

DETAILED DESCRIPTION OF THE PREFERRED EMBODIMENTS

The invention will be explained in detail as follows.

According to the invention, the presence of an optically active α-amino acid containing a secondary amine and a metal ion in the reaction of a pyruvic acid of the following formula (1) (including a salt form) with an indole-3-pyruvic acid of the following formula (2) (including a salt form) induces asymmetry at the 4 position of 4-hydroxy-4-(3-indolylmethyl)-2-ketoglutaric acid of the following formula (3).

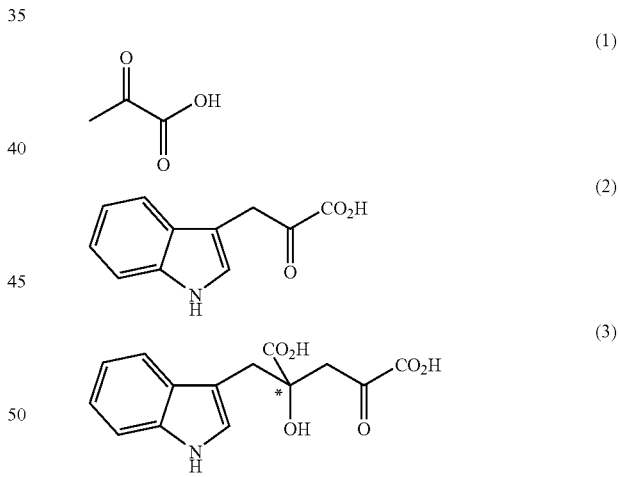

wherein the asterisk in the formula (3) indicates an asymmetric carbon.

The optically active α-amino acid containing a secondary amine used in the reaction of the invention is suitable as far as it is an optically active α-amino acid containing a carboxylic acid and a secondary amine. It may be either linear or cyclic, in a salt form or free form, and its optical isomer may be L- or D-isomer and in some circumstance contain an excess of the L-isomer or D-isomer. Specifically, it includes N-monoalkyl amino acids typified by N-monoalkylalanine, N-monoalkylserine, N-monoalkylglutamic acid, N-monoalkylaspartic acid, N-monoalkylthreonine, N-monoalkyllysine, N,S-dialkylcysteine (including its cyclic compounds) (wherein the alkyl group is of 1 to 3 carbons), or proline, hydroxyproline, pipecolic acid, and the like. In view of easy availability and high selectivity to the enantiomer, the structure of the following general formula (6) is preferred, and optically active cyclic α-amino acids containing a secondary amine are more preferred, and proline and hydroxyproline are even more preferred.

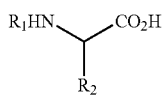

(6)

wherein $R_1$ represents an alkyl group having 1 to 3 carbon atoms; $R_2$ represents an alkyl group having 1-6 carbon atoms or an aralkyl group having 7 to 10 carbon atoms, in which the alkyl or aralkyl group may be substituted by at least one hydroxyl or amino group.

There is no limitation on the metal ion used in the invention as long as it forms a good complex with the optically active α-amino acid containing a secondary amine and the resulting complex is soluble in the reaction mixture. Specifically, it includes magnesium (II) ion, aluminum (III) ion, boron ion, zinc (II) ion, copper (I) ion, copper (II) ion, nickel (II) ion, cobalt (II) ion, cobalt (III) ion, iron (II) ion, iron (III) ion, manganese (II) ion, manganese (III) ion, palladium (I) ion, palladium (II) ion, platinum (IV) ion, and the like. In view of easy availability and having a high expected asymmetry-inducing effect, aluminum (III) ion, boron ion, magnesium (II) ion, zinc (II) ion, cobalt (II) ion, cobalt (III) ion, nickel (II) ion, palladium (I) ion, palladium (II) ion, and platinum (IV) ion are preferred, and magnesium (II) ion, zinc (II) ion, cobalt (II) ion, cobalt (III) ion, nickel (II) ion, platinum (IV) ion, and palladium (I) ion, and palladium (II) ion are more preferred. Magnesium (II) ion, zinc (II) ion, nickel (II) ion, cobalt (II) ion, and cobalt (III) ion are even more preferred, and zinc (II) ion and nickel (II) ion are particularly preferred.

Though there is no particular limitation in the ratio of the optically active α-amino acid containing a secondary amine to the metal ion used in the reaction of the invention as long as the reaction proceeds, the preferred molar ratio is 1 to 10 equimolar, and more preferably 2 to 8 equimolar, of amine to metal ion, since a too large ratio decreases the yield and a too small ratio decreases the selectivity for the enantiomer.

Though there is no particular limitation in the amount of pyruvic acid to be used to indole-3-pyruvic acid as long as the reaction proceeds, the preferred amount is 0.5 to 10 equimolar, more preferably 1 to 5 equimolar, of pyruvic acid to indole-3-pyruvic acid, in view of the reaction resulting in a good yield.

Though there is no particular limitation in the molar ratio of the optically active α-amino acid containing a secondary amine to indole-3-pyruvic acid so long as the reaction proceeds, the preferred ratio is 0.01 to 2 equimolar, and more preferably 0.05 to 0.5 equimolar, of amine to indole-3-pyruvic acid, since a too large ratio is economically disagreeable and a too small ratio decreases the yield and selectivity for the enantiomer.

Though there is no particular limitation of the reaction solvent so long as the reaction proceeds, preferably a polar solvent such as water, methanol, acetonitrile, dimethylformamide, and the like, or their mixture is used.

Though there is no particular limitation of the concentration of the indole-3-pyruvic acid in the reaction solvent so long as the reaction proceeds, the preferred concentration is 0.01 to 2.0 mol/L, more preferably 0.05 to 1.5 mol/L, since too high a concentration makes the operability worse and a too low a concentration is economically disagreeable.

In particular, there is no particular limitation on the pH when water or an aqueous organic solvent is used, so long as the reaction proceeds; the pH range is preferably in 5 to 13, and more preferably in 7 to 12, since the aldol reaction proceeds spontaneously at an excessively high pH and a decomposition reaction of the product occurs at a lower pH.

Though there is no limitation of the base to be used so long as the reaction proceeds, an inorganic base or organic amine compound is preferably used. From economical reasons, more preferably, a base such as lithium hydroxide, sodium hydroxide, lithium carbonate, potassium carbonate, calcium carbonate, triethylamine, morpholine, pyrrolidine, piperidine, ammonia, and the like is used.

Though there is no particular limitation in the reaction temperature employed so long as the reaction proceeds, the preferred temperature is −40 to 100° C., more preferably −20 to 50° C.

In one example of the invention, the aldol reaction mixture obtained contains 4-hydroxy-4-(3-indolylmethyl)-2-ketoglutaric acid in which asymmetry is induced at the 4 position. According to Example 2 described in WO2003/059865, said compound can be isolated and purified in an original form. In such a case, a variety of salts are formed depending on the kind of the base used in the reaction or the kind of the base used in a work-up and purification step. For example, the ammonium salt, lithium salt, sodium salt, potassium salt, calcium salt, magnesium salt, barium salt, and the like are preferred from an economical point of view, but the salt is not limited to them.

In one example of the invention, a transaminase and a proper amino-donor (L- or D-alanine, tryptophan, etc.) are permitted to act on the solution of the aldol reaction containing 4-hydroxy-4-(3-indolylmethyl)-2-ketoglutaric acid in which asymmetry is induced at the 4 position by the invention, allowing the direct enzymatic conversion into monatin. In this operation, the enzyme may be added at an early stage of the cross aldol reaction of the invention, and such an example is naturally incorporated in the present invention.

As for the transaminase, there is no particular limitation as far as it can transfer an amino group of the amino donor to 4-hydroxy-4-(3-indolylmethyl)-2-ketoglutaric acid. The transaminase can also be prepared as a cultured microorganisms that produce the enzyme.

Such microorganisms are, for example, those which belong to genus *Bacillus* or *Paenibacillus*. Concrete examples of such microorganisms are the following D-aminotransferase producing bacteria:

Bacillus sphaericus ATCC 10208,
Bacillus pulvifaciens AJ 1327,
Paenibacillus larvae susp. Pulvifaciens ATCC13537
Bacillus macerans AJ 1617,
Paenibacillus macerans ATCC 8244,
Bacillus lentus AJ 12699, and
Bacillus lentus ATCC 10840.

Among them, one example of transaminase that can be used for the present invention is a D-aminotransferase (SEQ ID NO:2) derived from *Bacillus macerans*. The D-aminotransferase and mutant enzymes thereof are described in the international publication WO2004/053125A1 by the present applicant in more detail, and the content thereof are incorporated herein by reference in its entirety. Briefly, a protein having the amino acid sequence represented by SEQ ID NO:2 is the protein having a D-aminotransferase activity derived from *Bacillus macerans* AJ 1617. *Bacillus macerans*

AJ 1617 has been deposited in the International Patent Organism Depositary, National Institute of Advanced Industrial Science and Technology (Central 6, 1-1-1 Higashi, Tsukubashi, Ibaraki Prefecture, 305-8566, Japan) on Dec. 13, 2001, as Accession number FERM BP-8243 (transferred to the International Deposition on Nov. 22, 2002, from FERM P-18653 that had been deposited on Dec. 13, 2001). A mutant enzyme (S243N/A182S), which has amino acid replacements in the amino acid sequence represented by SEQ ID NO:2 from alanine at position 182 to serine, and from serine at position 243 to asparagine is particularly preferable, since it has a high stereoselectivity to the 4R-isomer of the substrate, 4-hydroxy-4-(3-indolylmethyl)-2-ketoglutaric acid.

The amino donor used for the process of the present invention is not particularly limited to any specific compound, so long as it is an amino group-containing compound which can provide an amino group in an amino exchange reaction by transaminase, and can be determined by a preliminary test in accordance with each of the bacteria and isolated enzymes. In this case, an amino acid is often used. The amino acid may be any of naturally occurring or unnatural amino acids, and even more any of α-amino acids, β-amino acids, or γ-amino acids. Any of L-amino acid, D-amino acid, and DL-amino acid may be used. Such amino acids are not limited to, but are preferably amino acid such as glutamic acid, aspartic acid, alanine, tryptophan, phenylalanine, isoleucine, leucine, tyrosine, valine, arginine, asparagine, glutamine, methionine, ornithine, serine, cystein, histidine, and lysine. In terms of the production of (2R,4R)-monatin with high sweetening potency, a D-amino acid is more preferable. These may be used as a single species or a mixture of two or more.

The D-amino acid as an amino donor can be replaced by the combination of L-amino acid and/or DL-amino acid, and a racemase corresponding thereto. The racemase used for this purpose may include alanine racemase, glutamic acid racemase, aspartic acid racemase, and phenylalanine racemase. Specifically, L-alanine, L-glutamic acid, L-phenylalanine, L-aspartic acid or a racemic mixture of any of the above L-amino acids may be added to the reaction solution during the production of monatin.

In terms of the reproduction of pyruvic acid and indole-3-pyruvic acid after amination, which are starting materials for the aldol reaction, alanine and tryptophan is preferable, and alanine is more preferable. In terms of the production of (2R,4R)-monatin with a high sweetening potency, D-alanine and D-tryptophan are preferable, and D-alanine is more preferable. In order to provide an amino donor in situ from low-cost materials, the combination of L-alanine and/or DL-alanine, and alanine racemase is particularly preferable.

In one preferable example of the invention, a gene encoding the transaminase can be introduced into cells of microorganisms. There have been reported numerous examples for producing useful proteins such as enzymes and physiologically active substances by taking advantage of recombinant DNA technology. By the use of recombinant DNA technology, the useful protein which is naturally present in a trace amount can be produced on a large scale. Genes to be incorporated may include the genes L-aminotransferase and D-aminotransferase. In one example, D-aminotransferase from *Bacillus sphaericus* and *Bacillus macerans* can be introduced into mincroorganisms.

A D-aminotransferase gene derived from *Bacillus sphaericus* has been reported in European Patent Publication No. 0 736 604 and Taylor et al., *Journal of Bacteriol.*, 1998, vol. 180, no. 16, p. 4319, both of which are incorporated herein by reference in their entireties. As a D-aminotransferase gene derived from *Bacillus macerans*, the DNA consisting of the nucleotide sequence represented by SEQ ID NO: 1 can be used. When the D-aminotransferase gene represented by SEQ ID NO: 1 is used, the D-aminotransferase represented by SEQ ID NO:2 is obtained. Origins of the D-aminotransferase gene are not limited to such, but any genes encoding a D-aminotransferase that produces the target D-glutamic acid derivative can be used.

When the protein is produced on a large scale using the recombinant DNA technology, host cells to be transformed may include bacterial cells, actinomycetal cells, yeast cells, fungal cells, plant cells, and animal cells. Among them, findings on recombinant DNA operation have been accumulated as to microorganisms such as *Bacillus, Pseudomonas, Brevibacterium, Corynebacterium, Streptomyces*, and *Escherichia coli*. Generally, there are numerous findings for the techniques to produce the proteins on a large scale using the bacterial genus *Escherichia*, and thus the genus *Escherichia*, preferably *Escherichia coli* may be used.

The target transaminase gene may be introduced into these microorganisms using a vector such as plasmid and phage carrying the same, or the target gene may be integrated into a chromosome in the microbial cell by homologous recombination. Preferably, a plasmid vector of a multiple copy type may be used. Examples of the vector for *Escherichia coli* may include plasmids having a replication origin derived from Col E1, e.g., pUC type plasmid and pBR322 type plasmid or derivatives thereof. As a promoter for the expression of the target transaminase gene in these vectors, the promoter usually used for the protein production in *Escherichia coli* may be used. Examples thereof may include strong promoters such as a T7 promoter, trp promoter, lac promoter, tac promoter, and PL promoter. To increase the production, it is preferable to ligate a terminator which is a transcription termination sequence to the downstream of the protein gene. This terminator may include a T7 terminator, fd phage terminator, T4 terminator, terminator of tetracycline resistant gene, terminator of *Escherichia coli* trpA gene, and the like. In order to select transformants, it is preferred that the vector has a marker gene such as an ampicillin resistance gene. As such a plasmid, for example, expression vectors having a strong promoter such as pUC type (supplied from Takara Shuzo Co., Ltd.), pPRO type (supplied from Clontech), and pKK233-2 (supplied from Clontech) are commercially available.

The method for culturing the microorganism that produces the enzyme used for the amination reaction may be performed with a medium usually used in this field, i.e., a medium containing carbon sources, nitrogen sources, inorganic salts, trace metal salts, vitamins, and the like. Depending on the type of the microorganism or the culturing condition, it is also possible to promote an amino group transfer reaction activity by adding an amino compound such as an amino acid at about 0.1 to 1.0 g/dl to the medium.

When the recombinant cells are cultured, an agent such as ampicillin, kanamycin, neomycin, or chloramphenicol may be appropriately added corresponding to the selection marker of the vector. The expression of the recombinant gene may be increased by appropriately adding an inducer in accordance with the promoter loaded in the vector. For example, when a vector is constructed by ligating the target gene downstream of the lac promoter, it is possible to appropriately add isopropyl-1-thio-beta-D-galactopyranoside (IPTG) at a final concentration of 0.1 mM to 5 mM. Alternatively, in place of this, it is also possible to appropriately add galactose at a final concentration of 0.1 to 5 g/dl, desirably 0.5 to 2 g/dl. Specific substances for use as the ingredients of the above medium may include the following: Carbon sources are not limited as long as they are available for the microorganism to be employed, and examples thereof may include glucose, sucrose, fructose, glycerol, acetic acid, and the like, and mixtures thereof. Examples of nitrogen sources to be used may include ammonium sulfate, ammonium chloride, urea, yeast extract, meat extract, corn steep liquor, hydrolyzed casein, and mixtures thereof. An example of the specific medium composition may be the medium containing 0.5 g/dl of fumaric acid, 1 g/dl of yeast extract, 1 g/dl of peptone, 0.3 g/dl of ammonium sulfate, 0.3 g/dl of $K_2HPO_4$, 0.1 g/dl of $KH_2PO_4$, 1 mg/dl of $FeSO_4.7H_2O$, and 1 mg/dl of $MnSO_4.4H_2O$ (pH 7.0).

The cultivation may be performed within the range of the temperature where the microorganism used usually grows, i.e., within the range of 10 to 45° C., preferably 20 to 40° C., and more preferably 25 to 37° C. The pH value of the medium may be controlled within the range of preferably 2 to 12, more preferably 3 to 10, and still more preferably 4 to 8. An aeration condition may be set up as the condition suitable for growth of the microorganism used, and an aerobic condition is preferable. The culture period may be usually 12 to 120 hours, and preferably about 24 to 96 hours.

As used herein, "in the presence of enzyme" in the amination reaction means that the enzyme may be present in the reaction system in any form as long as the keto acid derivative may be converted to the glutamic acid derivative. For example, the enzyme alone may be added into the reaction system, or the microorganism having the relevant enzyme activity (enzyme producing bacteria or cells transformed with the recombinant DNA), the culture of the microorganism (liquid culture, solid culture, etc.), the cultured medium (from which microbial cells are removed), or the treated product of the culture may be added to the reaction system. When using the culture of the microorganism, the reaction may be performed as the microorganism is cultured, or the reaction may be performed using the culture previously prepared for obtaining the enzyme. The "treatment" herein means the treatment performed for the purpose of collecting the enzyme from the microbial cells, and may include, for example, the ultrasonic disruption, treatment with glass beads, French press, and lyophilization, and the treatment with bacteriolytic enzyme, organic solvent or surfactant. Substances which have been subjected to these treatments may further be processed by standard methods (liquid chromatography, ammonium sulfate fractionation, etc.) to prepare a crude fraction of the enzyme or a purified enzyme, which may be employed as long as it has a required property.

Moreover, the above culture or treated product may be used after entrapment in carrageenan and polyacrylamide or immobilizing it on a membrane of polyether sulfone or reproduced cellulose.

In the reaction system, a coenzyme, detergent, or an organic solvent may be included as an accelerating substance of the reaction. For example, a detergent such as Triton X and Tween or an organic solvent such as toluene and xylene may also be used in order to increase permeability of the substrate keto acid into the microbial cells. A coenzyme such as pyridoxal-5-phosphate as a reaction facilitating substance may also be added to the above medium.

When the step of the cultivation for producing the enzyme and the step of amination reaction are performed separately in a sequential manner, the latter step of amination reaction does not have to be performed in an aerobic atmosphere. Rather the reaction may be performed under an anaerobic atmosphere. The reaction may also be performed in a system where dissolved oxygen in the reaction liquid is eliminated by nitrogen gas substitution, argon gas substitution, addition of sodium sulfite, and the like. The reaction temperature may usually be within the range where the employed enzyme has the activity, i.e., is in the range of 10 to 50° C., more preferably 20 to 40° C. and still more preferably 25 to 37° C. The pH value of the reaction solution may be adjusted into the range of usually 2 to 12, preferably 6 to 11, and more preferably 7 to 9. The reaction time period may be usually about 1 to 120 hours, preferably about 1 to 72 hours, and more preferably about 1 to 24 hours.

In the present invention, the aldol condensation reaction for producing 4-hydroxy-4-(3-indolylmethyl)-2-ketoglutaric acid, and the reaction for conveting the product to monatin with the transaminase can be performed simultaneously or sequentially.

In one embodiment of the present invention, an amine derivative of the following general formula (4) or its salt is permitted to act on the solution of the aldol reaction containing 4-hydroxy-4-(3-indolylmethyl)-2-ketoglutaric acid of the following formula (3) in which asymmetry is induced at the 4 position, allowing the formation of 4-hydroxy-4-(3-indolylmethyl)-2-hydroxyiminoglutaric acid of the following formula (5) or its salt in which asymmetry is induced at the 4 position; this may further be isolated.

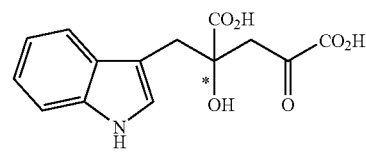
(3)

wherein the asterisk in the formula (3) indicates an asymmetric carbon at the 4 position.

$NH_2OR$ (4)

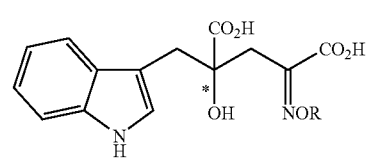
(5)

wherein the asterisk in the formula (5) indicates an asymmetric carbon at the 4 position.

The amine derivative of the invention has the structure of the general formula (4).

$NH_2OR$ (4)

The substituent R in the general formula (4) is removed in a reductive condition during the conversion into monatin; thus, there is no particular limitation in R as far as the reaction proceeds, and for example, R includes hydrogen atom, methyl, ethyl, benzyl groups, and the like, because these are commercially easily available. In view of the easiness of elimination outside the system and from an economical point of view, a hydrogen atom or methyl group is preferred.

Though there is no particular limitation on the molar ratio of the amine derivative to indole-3-pyruvic acid so long as the reaction proceeds, the ratio is preferably 1 to 10 equimolar, and more preferably 2 to 5 equimolar, amine derivative to indole-3-pyruvic acid, since a large quantity is economically disagreeable and a small quantity results in incomplete reaction.

In a process for reacting an amine derivative with 4-hydroxy-4-(3-indolylmethyl)-2-ketoglutaric acid in which asymmetry is induced at the 4 position obtained by the invention, the latter may be once isolated and separately reacted with the amine derivative in a reaction solvent which may be used for the latter, or alternatively the amine may be added directly to the solution of aldol reaction containing the latter. Since the decomposition of 4-hydroxy-4-(3-indolylmethyl)-2-ketoglutaric acid in which asymmetry is induced at the 4 position is suppressed to a minimum, it is preferred conveniently and industrially to directly add the amine to the solution of aldol reaction containing the latter.

It is necessary for the amine derivative to act on a reaction mixture in the pH range, preferably pH 4 to 13, more preferably pH 7 to 10, in which 4-hydroxy-4-(3-indolylmethyl)-2-ketoglutaric acid exists in a stable state.

A solution of the amine derivative may be adjusted at pH 7 to 10 in advance of adding the amine derivative, and then added to a solution containing 4-hydroxy-4-(3-indolylmethyl)-2-ketoglutaric acid, or alternatively the pH may be adjusted immediately after addition of the amine derivative. Since a drastic change of pH can be prevented and suppression of the decomposition of 4-hydroxy-4-(3-indolylmethyl)-2-ketoglutaric acid and increase of the yield are expected, it is preferred as a method that a solution of the amine derivative adjusted at pH 7 to 10 is prepared in advance, and then added to a solution containing 4-hydroxy-4-(3-indolylmethyl)-2-ketoglutaric acid.

The resulting 4-hydroxy-4-(3-indolylmethyl)-2-hydroxyiminoglutaric acid in which asymmetry is induced at the 4 position can be isolated in a variety of salt forms. For example, the ammonium salt, a chiral amine such as R-(+)- or S-(−)-1-phenethylamine, lithium salt, sodium salt, potassium salt, calcium salt, magnesium salt, barium salt, and the like are preferred from an economical point of view, but the invention is not limited to them. These may further be recrystallized in a conventional way to enhance the optical purity. For example, as shown in Example 20 and Example 23 in WO2003/059865 (which is incorporated herein by reference in its entirety), it may be recrystallized as the salt with R-(+)- or S-(−)-1-phenethylamine to efficiently enhance the optical purity.

Though there is no particular limitation in the solvent used in recrystallization, ammonia water, water, methanol, ethanol, propanol, butanol, ethyl acetate, methyl acetate, propyl acetate, butyl acetate, pentane, hexane, diethyl ether, toluene, and the like or a mixture of two or more of them are included. Preferably, ammonia water, water, methanol, ethanol, propanol, or a mixture of two or more of them is included. More preferably, water, ammonia water, ethanol, or mature of two or more of them is included.

The resulting optically pure 4-hydroxy-4-(3-indolylmethyl)-2-hydroxyiminoglutaric acid may be converted into monatin by catalytic hydrogenation according to Example 8 in WO2003/059865, which is incorporated herein by reference in its entirety.

Monatin and its analogues prepared by carrying out or through the process of the invention may be obtained in some cases in a form of respective stereoisomers (optical isomers) or of optically plural mixtures. The product obtained in an optically mixing form can be used itself as a sweetener component, or further purified in a known optical resolution method to yield an optically highly pure product. Thus, the purified monatin or its salts or analogues are applicable to the products produced in the process of the invention as far as they are produced through the process of the invention.

Preferably, the optically active compound of formula (3) or salt thereof formed by reacting the pyruvic acid of formula (1) with the indole-3-pyruvic acid of formula (2) in the presence of an optically active α-amino acid containing a secondary amine and a metal ion has an enantiomeric excess, ee, of at least 10%, more preferably at least 20%, even more preferably at least 40%, still more preferably at least 70%, and even still more preferably at least 90%.

Other features of the invention will become apparent in the course of the following descriptions of exemplary embodiments which are given for illustration of the invention and are not intended to be limiting thereof.

EXAMPLES

The followings will explain in order a method for preparing a sample from a reaction mixture for analysis (1 to 3), a method of determination of the yield (4 to 5), and a method of determination of enantiomeric excess (6).

Method for Preparing a Sample for Analysis

1) To a solution of aldol reaction containing 4-hydroxy-4-(3-indolylmethyl)-2-ketoglutaric acid is added an excess amount (about 4 equimolar amount for the used amount of indole-3-pyruvic acid) of hydroxyamine, and the mixture was adjusted to pH 7.0 to 10.0 by addition of 2N sodium hydroxide aqueous solution or 1N hydrochloric acid.

2) The mixture was stirred at room temperature overnight to form 4-hydroxy-4-(3-indolylmethyl)-2-hydroxyiminoglutaric acid.

3) A portion of the resulting reaction mixture was weighed and diluted with pure water in a mess-flask so that the concentration of 4-hydroxy-4-(3-indolylmethyl)-2-hydroxyiminoglutaric acid became 100 to 150 ppm; thus a sample for analysis was prepared.

Method of Determination of the Yield

4) The sample for analysis prepared in the above item 3) was applied to the following high performance liquid chromatography, and the yield was calculated by comparison in the percentage of the area of sample to that of a standard solution of 4-hydroxy-4-(3-indolylmethyl)-2-hydroxyiminoglutaric acid; thus, the yield (%) from indole-3-pyruvic acid used was calculated.

Analytical condition for high performance liquid chromatography (gradient)

Column: CAPCELL PAK C18 (MGII) 5 μm 4.6 mm×250 mm

Column temperature: 25° C.

Wavelength for detection: 210 nm

Flow rate: 1.0 ml/min

Mobile phase composition:

Solution A: $KH_2PO_4$ (20 mM)+$K_2HPO_4$ (20 mM) aqueous solution/acetonitrile=100/5

Solution B: $KH_2PO_4$ (20 mM)+$K_2HPO_4$ (20 mM) aqueous solution/acetonitrile=1/1

Injected amount of sample: 10 μL

Retention time: 11 minutes (4-hydroxy-4-(3-indolylmethyl)-2-hydroxyiminoglutaric acid)

Method of Determination of Enantiomeric Excess

5) The sample for analysis mentioned in the above item 3) was applied to the following high performance liquid chromatography, and on the basis of the peak integral value derived from the enantiomer at the 4 position of 4-hydroxy-4-(3-indolylmethyl)-2-hydroxyiminoglutaric acid, the selectivity and enantiomeric excess (% ee) of the enantiomer at the 4 position were calculated by the following procedure from the following equation:

Enantiomeric excess of the enantiomer at 4

=(Peak area of 4S-isomer−Peak area of 4R isomer)/ (Peak area of 4S-isomer+Peak area of 4R isomer)×100

(Regarded as % ee4S when the Sign is +, and % ee4R when the Sign is −)

Analytical condition for high performance liquid chromatography (gradient)

Column: SUMICHIRAL OA7100 4.6 mm×250 mm

Column temperature: 10° C.

Wavelength for detection: 210 nm

Flow rate: 0.5 ml/min

Mobile phase composition:

Solution A: $KH_2PO_4$ (20 mM)+$K_2HPO_4$ (20 mM) aqueous solution/acetonitrile=100/5

Solution B: $KH_2PO_4$ (20 mM)+$K_2HPO_4$ (20 mM) aqueous solution/acetonitrile=1/1

Injected amount of sample: 10 μL

Retention time: 19 min for 4R isomer; 21 min for 4S isomer

A complex solution was prepared according to the following method, the aldol reaction was performed at the respective pH, and the yield, enantiomer selectivity and enantiomeric excess were determined based on the content of 4-hydroxy-4-(3-indolylmethyl)-2-hydroxyiminoglutaric acid in the reaction mixture. Table 1 shows the results.

Preparation 1.

Preparation of an Aqueous Solution of Complex.

A solution of 0.36 g (2.0 mmol) of zinc acetate and 1.07 g (8.2 mmol) of trans-L-hydroxyproline dissolved in 25 ml of water was adjusted to pH 8.3 by addition of 2N sodium hydroxide aqueous solution to yield an aqueous solution of trans-L-hydroxyproline/zinc (II) complex.

Preparations 2-15

In the same manner as in Preparation 1, an aqueous solution of the complex was prepared using a metal salt and a variety of optically active amino acids containing a secondary amine as shown in Table 1. Table 1 shows the results.

TABLE 1

| Optically active α-amino acid containing secondary amine | | Metal Salt | |
|---|---|---|---|
| Name of Compound | mmol | Name of Compound | mmol |
| Prepn. 1 | trans-L-hydroxyproline | 8.2 | Zinc(II) acetate | 2.0 |
| Prepn. 2 | trans-L-hydroxyproline | 7.6 | Ni(II) chloride | 1.9 |
| Prepn. 3 | L-Proline | 8.7 | Zinc(II) acetate | 2.2 |
| Prepn. 4 | L-Proline | 1.9 | Ni(II) chloride | 2.1 |
| Prepn. 5 | L-Proline | 4.8 | Ni(II) chloride | 2.1 |
| Prepn. 6 | L-Proline | 6.2 | Ni(II) chloride | 2.1 |
| Prepn. 7 | L-Proline | 8.6 | Ni(II) chloride | 2.2 |
| Prepn. 8 | L-Proline | 21.6 | Ni(II) chloride | 2.2 |
| Prepn. 9 | N-Methyl-D-alanine | 8.4 | Ni(II) chloride | 1.9 |
| Prepn. 10 | L-Glutaric acid | 8.6 | Ni(II) chloride | 2.2 |
| Prepn. 11 | L-Lysine | 8.6 | Ni(II) chloride | 2.2 |
| Prepn. 12 | L-Phenylalanine | 8.6 | Ni(II) chloride | 2.2 |
| Prepn. 13 | L-Tartaric acid | 8.6 | Ni(II) chloride | 2.2 |
| Prepn. 14 | L-Proline | None | Ni(II) chloride | 2.2 |
| Prepn. 15 | L-Proline | 22.0 | Ni(II) chloride | None |

Example 1

Asymmetric Cross Aldol Reaction

Under an argon atmosphere, 0.21 g of indole-3-pyruvic acid was suspended in 5.0 ml of water, which was dissolved by addition of 2N sodium hydroxide aqueous solution and adjusted to pH 12. Then, the solution was adjusted to pH 7 to 10 by addition of 1N hydrochloric acid, and then sodium pyruvate (0.34 g) and the solution (1.0 ml) prepared in Preparation 1 were added. At this stage, the pH of the solution was confirmed with a pH meter, and if necessary the solution was adjusted to the prescribed pH with 2N sodium hydroxide aqueous solution or 1N hydrochloric acid. The mixture was stirred at room temperature for 5 hours, and the yield and enantiomeric excess of 4-hydroxy-4-(3-indolylmethyl)-2-hydroxyiminoglutaric acid in the reaction mixture were determined.

Examples 2-12 and Comparative Examples 1-6

In the same manner as in Example 1, the reaction was carried out at the pH, the complex solution, and the reaction time as indicated in Table 2, and the yield and enantiomeric excess (ee) of 4-hydroxy-4-(3-indolylmethyl)-2-hydroxyiminoglutaric acid in the reaction mixture were determined. Table 2 shows the results.

TABLE 2

| | pH in reaction mixture | Complex Solution (Table 1) | | React. time (h) | Analytical Value | |
|---|---|---|---|---|---|---|
| | | Solution used | Amount (ml) | | Yield (%) | ee at position 4 |
| Ex. 1 | 7.5 | Prep. 1 | 1.0 | 5.0 | 20 | 38% ee4R |
| Ex. 2 | 8.8 | Prep. 1 | 1.0 | 5.0 | 29 | 41% ee4R |
| Ex. 3 | 10.0 | Prep. 1 | 1.0 | 5.0 | 28 | 39% ee4R |
| Ex. 4 | 9.0 | Prep. 2 | 1.0 | 6.0 | 17 | 27% ee4S |
| Ex. 5 | 8.5 | Prep. 3 | 1.0 | 5.0 | 25 | 20% ee4R |
| Ex. 6 | 10.0 | Prep. 4 | 1.0 | 4.0 | 23 | 4% ee4S |
| Ex. 7 | 10.0 | Prep. 5 | 1.0 | 4.0 | 25 | 13% ee4S |
| Ex. 8 | 10.1 | Prep. 6 | 1.0 | 4.0 | 25 | 24% ee4S |
| Ex. 9 | 10.0 | Prep. 7 | 1.0 | 4.0 | 27 | 22% ee4S |
| Ex. 10 | 9.7 | Prep. 7 | 1.0 | 1.5 | 23 | 29% ee4S |
| Ex. 11 | 10.0 | Prep. 8 | 1.0 | 4.0 | 14 | 26% ee4S |
| Ex. 12 | 9.0 | Prep. 9 | 1.0 | 5.0 | 33 | 12% ee4S |
| C.E. 1 | 9.1 | Prep. 10 | 1.0 | 5.0 | <5 | 0 |
| C.E. 2 | 8.6 | Prep. 11 | 1.0 | 5.0 | <5 | 0 |
| C.E. 3 | 8.4 | Prep. 12 | 1.0 | 5.0 | <5 | 0 |
| C.E. 4 | 7.7 | Prep. 13 | 1.0 | 5.0 | <5 | 0 |
| C.E. 5 | 10.0 | Prep. 14 | 1.0 | 4.0 | 17 | 0 |
| C.E. 6 | 10.0 | Prep. 15 | 1.0 | 5.0 | 10 | 0 |

Ex. = Example; C.E. = Comparative Example; Prep. = Preparation.

It was found that when a zinc complex was used, the 4R isomer was selectively produced (Examples 1 to 3 and 5). It was also found that when a nickel complex was used, high selectivity was obtained for the 4S-isomer (Examples 4, 6 to 12). As for the relation between the optically active α-amino acid containing a secondary amine and the metal salt, it was observed that the selectivity for the enantiomer is poor at 1:1, and gradually improved at 2:1, 3:1, and 4:1, but in a large excess at 10:1, there was a trend to inhibit the yield (Examples 6 to 11). As for the optically active α-amino acids containing a secondary amine, there was a trend of showing high selectivity for the enantiomer with the cyclic amino acids such as proline or trans-L-hydroxyproline, in comparison with linear amino acids typified by N-methyl-D-alanine (Examples 4, 9, and 12). When an optically active α-amino acid containing primary-amine was used, in every case, no selectivity for the enantiomer was observed, and the yield was very low (Comparative Examples 1 to 3). Similarly, when L-tartaric acid which is known to form favorable complexes with metal ions, was used no selectivity for the enantiomer was observed, too (Comparative Example 4). Thus, from Comparative Examples 1 to 4, it is understood that a secondary amine is essential for the molecular structure not only for occurrence of selectivity for the enantiomer but also in the course of reaction. In addition, since no selectivity for the enantiomer occurs in the presence of a nickel (II) ion alone or L-proline alone, it is considered that the coexistence of a metal ion and an optically active amino acid containing a secondary amine in the reaction mixture is essential for occurrence of selectivity for the enantiomer.

Example 13

Solvent Effect

In place of water as solvent, 5 ml of methanol was used, but otherwise the experiment was carried out in the same manner as in Example 2. Analysis of the reaction mixture indicated that 4-hydroxy-4-(3-indolylmethyl)-2-hydroxyiminoglutaric acid was formed in 19% (enantiomeric excess 19%; selectivity for the 4-R isomer). From this result, it was found that water is better than methanol in yield and enantiomeric excess (Examples 2 and 13).

Example 14

Effect of Bases

Under an argon atmosphere, 1.00 g of indole-3-pyruvic acid was suspended in 15.0 ml of water, which was then added with 1.72 ml of morpholine (4 fold molar excess to indole-3-pyruvic acid) and the complex solution (6.0 ml) prepared in Preparation 1 (Table 1). At this stage, the pH of the reaction mixture was 7.1. After stirring at room temperature for 5 hours, the yield and enantiomeric excess of 4-hydroxy-4-(3-indolylmethyl)-2-hydroxyiminoglutaric acid in the reaction mixture were determined.

Example 15 and Comparative Example 7

In the same manner as in Example 14, the reaction was carried out with the pH, the base, the complex solution, and the reaction time as indicated in Table 3, and the yield and enantiomeric excess of 4-hydroxy-4-(3-indolylmethyl)-2-hydroxyiminoglutaric acid in the reaction mixture were determined. Table 3 shows the results.

TABLE 3

| | pH in reaction mixture | Base | Complex Solution (Table 1) Solution used | Amount (ml) | React. time (h) | Analytical Value Yield (%) | Enantiomeric excess at position 4 |
|---|---|---|---|---|---|---|---|
| Ex. 14 | 7.1 | morpholine | Prep. 1 | 6.0 | 5.0 | 25 | 27% ee4R |
| Ex. 15 | 7.8 | pyrrolidine | Prep. 1 | 6.0 | 5.0 | 30 | 14% ee4R |
| C.E. 7 | 6.7 | morpholine | — | — | 6.0 | 0 | 0 |

Ex. = Example;
C.E. = Comparative Example;
Prep. = Preparation

It was found that when morpholine or pyrrolidine were used as a base instead of sodium hydroxide, the enantiomer selectivity at position 4 was reduced, even though the yield of 4-hydroxy-4-(3-indolylmethyl)-2-hydroxyiminoglutaric acid was equal. In the case of Comparative Example 7 without addition of the Complex Solution, the reaction of interest did not proceed at all, suggesting that the Complex Solution is essential for the progress of reaction.

Example 16

Purification by Crystallization with an Amine Derivative

The above experiment in Example 2 was carried out on a 24-fold scale to prepare an aldol reaction mixture containing 4-hydroxy-4-(3-indolylmethyl)-2-hydroxyiminoglutaric acid. The resulting aldol reaction mixture was adjusted to pH 1.2 by addition of 12N hydrochloric acid and extracted twice with ethyl acetate (100 ml×2). The organic layer was washed with saturated brine, dried with anhydrous magnesium sulfate, filtered to remove the magnesium sulfate, and concentrated with an evaporator to yield the residue. 28% Ammonia water (20 ml) was added, and then 200 ml of ethanol was added, and the mixture was preserved at 5° C. for 3 days. The precipitated crystals were collected by filtration and dried under reduced pressure to yield 4-hydroxy-4-(3-indolylmethyl)-2-hydroxyiminoglutaric acid diammonium salt (2.2 g)(purity 88%; yield 23%). The selectivity for the enantiomer was 44% ee for the 4R isomer.

NMR Spectrum $^1$HNMR (DMSO-$d_6$) d: 2.66 (s, 2H), 2.89 (d, J=14.4 Hz, 1H), 3.04 (d, J=14.4 Hz, 1H), 6.89-6.94 (m, 1H), 6.97-7.03 (m, 1H), 7.11 (d, J=2.8 Hz, 1H), 7.27 (d, J=7.8 Hz, 1H), 7.53 (d, J=7.8 Hz, 1H), 10.71 (br s, 1H).

Mass Spectrum

ESI-MS Calcd. for $C_{14}H_{14}N_2O_6$=306.28. Found: 305.17 (MH$^-$).

Example 17

Enzymatic Conversion to Monatin

A solution of 0.36 g (2.0 mmol) of zinc acetate and 1.07 g (8.2 mmol) of trans-L-hydroxyproline dissolved in 20 ml of water was adjusted at pH 8.3 by addition of 2N sodium hydroxide aqueous solution to yield an aqueous solution of trans-L-hydroxyproline/zinc (II) complex.

5.0 g of indole-3-pyruvic acid was suspended in 100 ml of water, which was dissolved by addition of 2N sodium hydroxide aqueous solution and adjusted to pH 12. Then, the solution was adjusted to pH 9 by addition of 1N hydrochloric acid, and then sodium pyruvate (8.12 g) and the solution of trans-L-hydroxyproline/zinc (II) complex (22 ml) were added. The mixture was stirred at room temperature for 4 hours, and the cross-aldol reaction was performed. To 25 ml of the obtained reaction mixture, D-Ala (1.8 g) and pyridoxal-5'-phosphate (1 mg) were added, and then 0.5 g of BMDAT-expressing $E.$ $coli$ or S243N/A182S mutant BMDAT-expressing $E.$ $coli$ was added in suspension to carry out amination reaction at 33° C. for 24 hours. By HPLC analysis of the reaction mixture with appropriate dilution, it was confirmed to genarate (2R,4R)-monatin or (2R,4S)-monatin as shown in Table 4. Incidentally, the BMDAT-expressing $E.$ $coli$ and S243N/A182S mutant BMDAT-expressing $E.$ $coli$ used for the amination reaction were prepared according to the method described in the following Reference Example.

TABLE 4

| | (2R,4R)-monatin (mM) | (2R,4S)-monatin (mM) | Yield of (2R,4R)-monatin based on IPA (%) |
|---|---|---|---|
| BMDAT | 10 | 0.83 | 4 |
| S243N/A182S | 7.5 | ND | 3 |

IPA = indole-3-pyruvic acid

Reference Example 1

Preparation of $E.$ $coli$ that Expresses D-Aminotransferase (BMDAT) Derived from $Bacillus$ $macerance$ Strain AJ1617

(1) Preparation of BMDAT-Expressing $E.$ $coli$

An expression plasmid pUCBMDAT was constructed according to the method described in WO2004/053125A1 (international publication date: Dec. 9, 2003), which is incorporated herein by reference in its entirety, in which the D-aminotransferase gene derived from $Bacillus$ $macerance$ strain AJ1617 (bmdat gene) was ligated downstream of the lac promoter of pUC18.

Briefly, 1 unit of restriction enzyme EcoRI was added to 30 µg of chromosomal DNA derived from $Bacillus$ $macerance$ strain AJ 1617, and incubated at 37° C. for 3 hours to perform partial digestion. Subsequently, fragments of 3 to 6 kbp were collected from this partially digested DNA by agarose gel electrophoresis. These DNA fragments were ligated to 1 µg of EcoRI-digested fragment of plasmid pUC18 (already treated with BAP, supplied from Takara Shuzo Co., Ltd.). The ligation mixture was used for transformation of $E.$ $coli$ JM109, and a colony of ampicillin resistance that has the target plasmid was selected, which was designated as pUCBMDAT. The open reading frame of the bmdat gene is about 850 bp, which corresponds to the region from position 630 to position 1481 of the nucleotide sequence of SEQ ID NO: 1

$E.$ $coli$ transformants having pUCBMDAT were inoculated on to 50 ml of casamino acid medium (0.5 g/dl of ammonium sulfate, 0.14 g/dl of $KH_2PO_4$, 0.23 g/dl of citrate 2Na.3$H_2O$, 0.1 g/dL of $MgSO_4.7H_2O$, 2 mg/dL of $FeSO_4$, mg/dL of $MnSO_4$, 2 mg/dL of pyridoxine hydrochloride, 0.1 mg/dL of thiamine, 1 g/dL of casamino acid, 0.3 g/dL of glycerol, pH 7.5) containing 0.1 mg/ml of ampicillin and 0.1 mM of IPTG. The medium was then cultured with shaking at 37° C. for 16 hours. Cells were collected from the cultured medium and washed to prepare cells of the BMDAT-expressing $E.$ $coli$.

(2) Preparation of Mutant BMDAT-Expressing $E.$ $coli$.

A mutant BMDAT expression plasmid by S243N/A182S site-directed mutagenesis was prepared from the above obtained plasmid pUCBMDAT according to the method described in WO2004/053125A 1 (which is incorporated herein by reference in its entirety), using a Quick Change Site-directed Mutagenesis Kit supplied from Stratagene.

Briefly, the following oligo DNA primers for mutagenesis, S243N-S (SEQ ID NO:3) and S243N-AS (SEQ ID NO:4), and A182S-S (SEQ ID NO:5) and A182S-AS (SEQ ID NO:6) were designed and synthesized.

S243N-S: 5'-gaaatcattgtgtcgtctgtaaattctgaggttacgccag-3' (SEQ ID NO:3)

S243N-AS: 5'-ctggcgtaacctcagaatttacagacgacacaatgatttc-3' (SEQ ID NO:4)

A182S-S: 5'-gtgacagaatgctcttcatctaatgtttacggaattaaag-3' (SEQ ID NO:5)

A182S-AS: 5'-ctttaattccgtaaacattagatgaagagcattctgtcac-3' (SEQ ID NO:6)

The S243N mutation was firstly introduced. According to the manufacture's instructions, the mutated BMDAT expression plasmid pS243N was obtained by amplifying with the wild type BMDAT expression plasmid pUCBMDAT prepared in the above (1) as a template, and primers S243N-S and S243N-AS under the following conditions: (95° C. for 30 sec., 55° C. for one min. and 68° C. for 8 min.)×18 cycles.

Subsequently, the A182S mutation was introduced. Except for using the pS243N as a template and primers A182S-S and A182S-AS, the reaction was performed according to the same method described above. Thus prepared plasmid pS243N/A182S was introduced into $E.$ $coli$ JM109 as the same method described above, and prepared cells of the S243N/A182S mutant BMDAT-expressing $E.$ $coli$.

INDUSTRIAL APPLICABILITY

It is very significant that a process for making the enantiomer selectivity occur in the cross aldol reaction in the invention allows the industrially efficient production of an important intermediate to monatin which is known as a sweetener.

It should be noted that other objects, features and aspects of the present invention will become apparent in the entire disclosure and that modifications from the disclosed examples may be done without departing the scope of the present invention claimed as appended herewith.

Also it should be noted that any combination of the disclosed and/or claimed elements, matters and/or items may fall under the modifications aforementioned.

Where a numerical limit or range is stated herein, the endpoints are included. Also, all values and subranges within a numerical limit or range are specifically included as if explicitly written out.

Obviously, numerous modifications and variations of the present invention are possible in light of the above teachings.

It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for producing an optically active compound of formula (3) or a salt thereof:

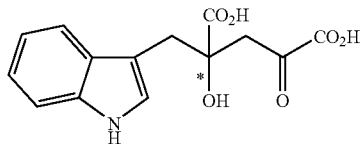

wherein the asterisk * in formula (3) indicates an asymmetric carbon,
said process comprising:
(a) reacting a pyruvic acid of formula (1)

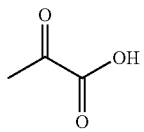

with an indole-3-pyruvic acid of formula (2)

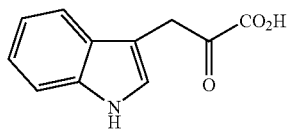

in the presence of at least one optically active α-amino acid containing a secondary amine and at least one metal ion.

2. A process for producing an optically active compound of formula (5) or a salt thereof:

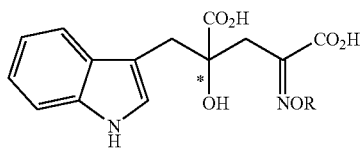

wherein the asterisk * in formula (5) indicates an asymmetric carbon,
said process comprising:
(a) reacting a compound of formula (4) or a salt thereof

NH$_2$OR  (4)

wherein R represents a hydrogen atom or methyl group
with said optically active compound of formula (3) obtained by the process of claim 1.

3. The process of claim 1, wherein said at least one optically active α-amino acid containing a secondary amine is one or more members selected from the group consisting of hydroxyproline, proline, and a mixture thereof.

4. The process of claim 1, wherein said at least one optically active α-amino acid containing a secondary amine is at least one compound represented by formula (6)

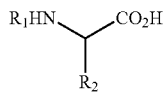

wherein $R_1$ represents an alkyl group having 1 to 3 carbon atoms; $R_2$ represents an alkyl group having 1 to 6 carbon atoms or an aralkyl group having 7 to 10 carbon atoms, in which the alkyl or aralkyl group may be substituted by at least one hydroxyl or amino group.

5. The process of claim 1, wherein said at least one metal ion is one or more selected members selected from the group consisting of magnesium (II) ion, zinc (II) ion, cobalt (II) ion, cobalt (III) ion, nickel (II) ion, and a mixture thereof.

6. The process of claim 1, wherein said reacting is carried out at a pH of 7 to 12.

7. A process for producing monatin or a salt thereof, which comprises:
(a) reacting a pyruvic acid of formula (1)

with an indole-3-pyruvic acid of formula (2)

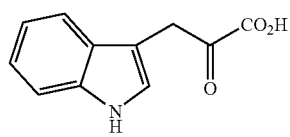

in the presence of at least one optically active α-amino acid containing a secondary amine and at least one metal ion, to obtain an optically active compound of formula (3) or a salt thereof:

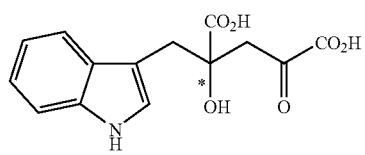

wherein the asterisk * in formula (3) indicates an asymmetric carbon; and
(b) converting said optically active compound of formula (3) or a salt thereof to monatin or a salt thereof.

8. The process of claim 7, wherein said at least one optically active α-amino acid containing a secondary amine is one or more members selected from the group consisting of hydroxyproline, proline, and a mixture thereof.

9. The process of claim 7, wherein said at least one optically active α-amino acid containing a secondary amine is at least one compound represented by formula (6)

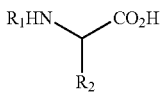
(6)

wherein $R_1$ represents an alkyl group having 1 to 3 carbon atoms; $R_2$ represents an alkyl group having 1 to 6 carbon atoms or an aralkyl group having 7 to 10 carbon atoms, in which the alkyl or aralkyl group may be substituted by at least one hydroxyl or amino group.

10. The process of claim 7, wherein said at least one metal ion is one or more selected members selected from the group consisting of magnesium (II) ion, zinc (II) ion, cobalt (II) ion, cobalt (III) ion, nickel (II) ion, and a mixture thereof.

11. The process of claim 7, wherein said reacting is carried out at a pH of 7 to 12.

12. The process of claim 7, wherein said converting said optically active compound of formula (3) or a salt thereof to monatin or a salt thereof comprises reacting said optically active compound of formula (3) with a transaminase and an amino donor.

13. The process of claim 12, wherein said at least one optically active α-amino acid containing a secondary amine is one or more members selected from the group consisting of hydroxyproline, proline, and a mixture thereof.

14. The process of claim 12, wherein said at least one optically active α-amino acid containing a secondary amine is at least one compound represented by formula (6)

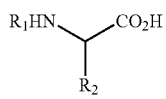
(6)

wherein $R_1$ represents an alkyl group having 1 to 3 carbon atoms; $R_2$ represents an alkyl group having 1 to 6 carbon atoms or an aralkyl group having 7 to 10 carbon atoms, in which the alkyl or aralkyl group may be substituted by at least one hydroxyl or amino group.

15. The process of claim 12, wherein said at least one metal ion is one or more selected members selected from the group consisting of magnesium (II) ion, zinc (II) ion, cobalt (II) ion, cobalt (III) ion, nickel (II) ion, and a mixture thereof.

16. The process of claim 12, wherein said reacting is carried out at a pH of 7 to 12.

* * * * *